US010058076B2

(12) United States Patent
Han et al.

(10) Patent No.: US 10,058,076 B2
(45) Date of Patent: Aug. 28, 2018

(54) METHOD OF MONITORING INFECTIOUS DISEASE, SYSTEM USING THE SAME, AND RECORDING MEDIUM FOR PERFORMING THE SAME

(71) Applicant: Foundation of Soongsil University-Industry Cooperation, Seoul (KR)

(72) Inventors: Youngjoon Han, Seoul (KR); Cheongshim Ko, Seoul (KR); Namki Lee, Seoul (KR); Hwanik Chung, Seoul (KR); Seungmo Hong, Seoul (KR); Youngtak Kim, Anyang-si (KR)

(73) Assignee: Foundation of Soongsil University-Industry Cooperation, Seoul (KR)

( * ) Notice: Subject to any disclaimer, the term of this patent is extended or adjusted under 35 U.S.C. 154(b) by 565 days.

(21) Appl. No.: 14/506,402

(22) Filed: Oct. 3, 2014

(65) Prior Publication Data
US 2015/0327518 A1 Nov. 19, 2015

(30) Foreign Application Priority Data
May 14, 2014 (KR) ........................ 10-2014-0057871

(51) Int. Cl.
*H04N 7/18* (2006.01)
*A01K 29/00* (2006.01)
(Continued)

(52) U.S. Cl.
CPC ............ *A01K 29/005* (2013.01); *A01K 29/00* (2013.01); *A61D 17/00* (2013.01); *G06F 19/00* (2013.01);
(Continued)

(58) Field of Classification Search
CPC .. A01K 29/005; A01K 29/00; G06F 19/3493; H04N 7/183; A61D 17/00; G01N 33/54366
(Continued)

(56) References Cited

U.S. PATENT DOCUMENTS 8,755,570 B2 * 6/2014 Gomas ................. G06K 9/6209
382/110
2007/0239723 A1 * 10/2007 Roybal .................. G06Q 50/02
(Continued)

FOREIGN PATENT DOCUMENTS

KR  10-2011-0030888 A  3/2011
KR  2011-0029760 A     3/2011
(Continued)

*Primary Examiner* — Y Lee
*Assistant Examiner* — Richard Carter
(74) *Attorney, Agent, or Firm* — Novick, Kim & Lee, PLLC; Sang Ho Lee

(57) ABSTRACT

A method of monitoring an infectious disease, a system using the same, and a recording medium for performing the same are provided. The infectious disease monitoring system includes an imaging device for capturing and transmitting image data on animals managed in a barn, a first server for determining whether a subject suspected of having an infectious disease is detected from the image data and, when the subject suspected of having the infectious disease is detected, transmitting a signal along with the image data, a second server for confirming an occurrence of the infectious disease by analyzing the image data of the subject suspected of having the infectious disease, and transmitting a warning signal when confirmed the occurrence of the infectious disease, and a manager terminal for requesting the image data on the animals to the first server upon receipt of the warning signal and displaying the image data.

12 Claims, 11 Drawing Sheets

(51) Int. Cl.
*A61D 17/00* (2006.01)
*G16H 50/80* (2018.01)
*G06F 19/00* (2018.01)
*G01N 33/543* (2006.01)

(52) U.S. Cl.
CPC ............ *G16H 50/80* (2018.01); *H04N 7/183* (2013.01); *G01N 33/54366* (2013.01); *Y02A 90/24* (2018.01)

(58) Field of Classification Search
USPC .................. 348/143; 342/450; 705/2, 317
See application file for complete search history.

(56) References Cited

U.S. PATENT DOCUMENTS

2009/0058730 A1* 3/2009 Geissler ............... A01K 11/004
342/450
2013/0138451 A1* 5/2013 Shiono .................. G06F 19/34
705/2
2013/0275316 A1* 10/2013 Teng .................... G06Q 30/018
705/317

FOREIGN PATENT DOCUMENTS

| KR | 10-2013-0128120 A | 11/2013 |
|----|-------------------|---------|
| KR | 10-2014-0013425 A | 2/2014  |
| KR | 10-1382627 B1     | 4/2014  |

* cited by examiner

METHOD OF MONITORING INFECTIOUS DISEASE, SYSTEM USING THE SAME, AND RECORDING MEDIUM FOR PERFORMING THE SAME

CROSS-REFERENCE TO RELATED APPLICATION

This application claims priority to and the benefit of Korean Patent Application No. 2014-0057871, filed on May 14, 2014, the disclosure of which is incorporated herein by reference in its entirety.

BACKGROUND OF INVENTION

The present invention relates to a method of monitoring an infectious disease, a system using the same, and a recording medium for performing the same, and more specifically, to a method of monitoring an infectious disease in order to monitor whether the infectious disease has occurred, a system using the same, and a recording medium for performing the same.

In general, animals raised in barns are wild animals that have been domesticated and improved by humans and are useful for human life to provide livestock products and labor. The animals raised in barns include birds such as poultry and livestock which narrowly refer only to such mammals. The poultry includes chickens, ducks, and the like, and the livestock include pigs, cattle, cows, horses, goats, and the like.

As industries develop, the livestock industry is also developing. According to the development of the livestock industry, massive numbers of poultry and livestock are being raised in barns.

However, as described above, when massive numbers of poultry and livestock are raised in barns, if an infectious disease occurs, animals raised in the barns are killed at the same time, which results in serious financial losses for livestock farms.

In order to address the above problem, livestock farmers manually check fever or abnormal symptoms of animals trapped in the barn in the related art. Such work wastefully consumes time and requires excessive human resources.

As a result, there is an urgent necessity to use advanced strategies in livestock disease management, identify diseases early on, and respond quickly in such management.

SUMMARY OF THE INVENTION

The present invention provides an infectious disease monitoring system, including a first server configured to determine whether there is a subject suspected of having the infectious disease in animals in a barn from image data received from an imaging device and transmit a suspected symptom occurrence signal along with image data on the object; a second server configured to receive the suspected symptom occurrence signal from the first server, re-diagnose occurrence of the infectious disease based on the image data on the subject suspected of having the infectious disease, and transmit a warning signal; and a manager terminal configured to receive the warning signal, request image data on the animal, and display the image data on the animal.

The present invention also provides a method of monitoring an infectious disease, including extracting an animal subject showing a behavior pattern related to the infectious disease as a candidate subject by detecting and tracking the animal subject in image data on animals, extracting a subject suspected of having the infectious disease by determining whether an appearance of the candidate subject matches an external lesion related to the infectious disease, and transmitting a signal indicating the extraction to an external server.

According to an aspect of the present invention, there is provided an infectious disease monitoring system. The system includes an imaging device configured to capture and transmit image data on animals managed in a barn; a first server configured to determine whether there is a subject suspected of having the infectious disease from the image data received from the imaging device and transmit a suspected symptom occurrence signal along with the image data on the subject suspected of having the infectious disease when there is the subject suspected of having the infectious disease; a second server configured to re-diagnose occurrence of the infectious disease by analyzing the image data on the subject suspected of having the infectious disease when the suspected symptom occurrence signal is received from the first server, and transmit a warning signal when it is determined that the infectious disease has occurred based on the re-diagnosis result; and a manager terminal configured to request image data on the animal from the first server when the warning signal is received from the second server and display the image data on the animal.

The first server may include an object detecting unit configured to detect at least one animal subject from the image data received from the imaging device; a candidate subject extracting unit configured to track the detected animal subject and extract an animal subject showing a predetermined behavior pattern related to the infectious disease as a candidate subject; a subject suspected of having the infectious disease extracting unit configured to determine whether image data on an appearance of the candidate subject matches an external lesion related to the infectious disease and extract a candidate subject matching the external lesion as a subject suspected of having the infectious disease; and an infectious-disease-suspicious sign signal generating unit configured to generate the suspected symptom occurrence signal including image data on the subject suspected of having the infectious disease when the subject suspected of having the infectious disease is extracted.

The candidate subject extracting unit may calculate an amount of activity of the animal subject during a specific time period and extract an animal subject having the calculated amount of activity equal to or less than a reference value as the candidate subject.

The second server may transmit the warning signal when a similarity with the infectious disease is a predetermined value or more based on an analysis result of the image data on the subject suspected of having the infectious disease.

The second server may transmit the warning signal in further consideration of location information of the barn in which the subject suspected of having the infectious disease is extracted.

The second server may transmit the warning signal when the barn in which the subject suspected of having the infectious disease is extracted is located in a zone that is at risk from an area in which an infectious disease has already occurred.

The manager terminal may transmit an infectious disease occurrence alarm to a device of a predetermined infectious disease-related organization when a definite diagnosis of infectious disease occurrence is determined based on the displayed image data on the animal is received from a manager.

According to another aspect of the present invention, there is provided a method of monitoring an infectious disease in which occurrence of an infectious disease of an animal raised in a barn is monitored. The method includes receiving image data on the animal in the barn from an imaging device; detecting at least one animal subject in the image data; tracking the detected animal subject and extracting an animal subject showing a predetermined behavior pattern related to the infectious disease as a candidate subject; determining whether image data on the candidate subject matches at least one external lesion related to the infectious disease and extracting a candidate subject matching the external lesion as a subject suspected of having the infectious disease; and transmitting a signal indicating that the subject suspected of having the infectious disease is extracted in the barn to an external server.

In the extracting of the animal subject having the predetermined behavior pattern as the candidate subject, an amount of activity of the animal subject during a specific time period may be calculated, and an animal subject having the calculated amount of activity equal to or less than a reference value may be extracted as the candidate subject.

According to still another aspect of the present invention, there is provided a computer readable recording medium recording a computer program for monitoring an infectious disease.

BRIEF DESCRIPTION OF THE DRAWINGS

The above and other objects, features, and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Detailed descriptions of the invention will be made with reference to the accompanying drawings illustrating specific embodiments of the invention as examples. These embodiments will be described in detail such that the invention can be performed by those skilled in the art. It should be understood that various embodiments of the invention are different but are not necessarily mutually exclusive. For example, a specific shape, structure, and characteristic of an embodiment described herein may be implemented in another embodiment without departing from the scope and spirit of the invention. In addition, it should be understood that a position or an arrangement of each component in each disclosed embodiment may be changed without departing from the scope and spirit of the invention. Accordingly, there is no intent to limit the invention to detailed descriptions to be described below. The scope of the invention is defined by the appended claims and encompasses all equivalents that fall within the scope of the appended claims. Like numbers refer to the same or like functions throughout the description of the figures.

Hereinafter, exemplary embodiments of the present invention will be described in greater detail with reference to the accompanying drawings.

Figure 1:
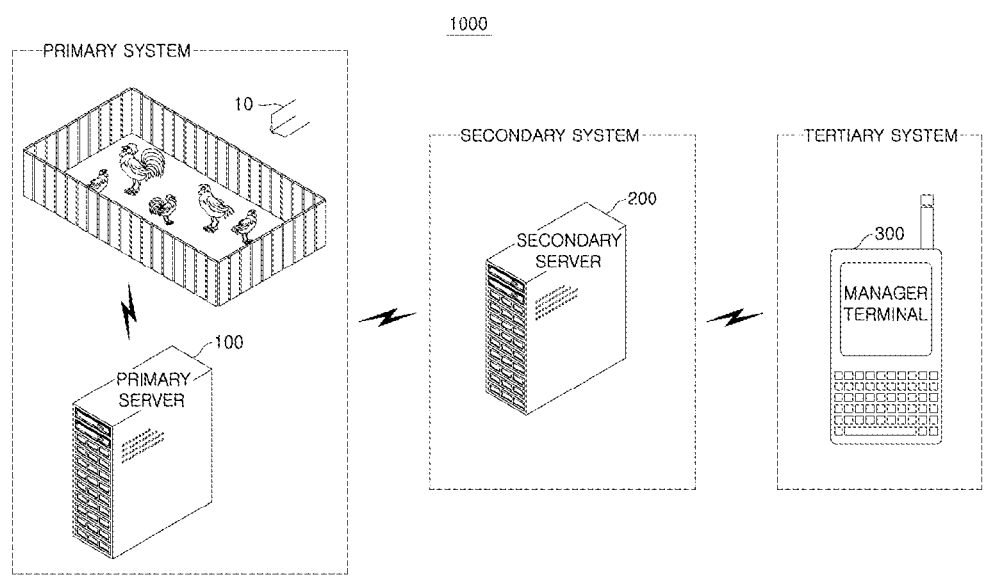
FIG. 1 is a diagram illustrating an infectious disease monitoring system according to an embodiment of the present invention.

FIG. 1 is a diagram illustrating an infectious disease monitoring system according to an embodiment of the present invention.

An infectious disease monitoring system 1000 includes a primary system configured to primarily detect whether animals are affected with an infectious disease in a field in a barn, a secondary system configured to perform wired and/or wireless communication with the primary system and secondarily analyze whether the infectious disease has occurred in the barn of the primary system, and a tertiary system configured to issue a final infectious disease occurrence alarm.

The primary system includes a device including an imaging device, a lighting device, and the like and configured to observe animals in the barn and a first server capable of communicating with the imaging device.

An imaging device 10 is installed in the barn in which animals are raised and captures behaviors of animals in the barn for 24 hours. At least one imaging device 10 is provided in the barn and generates image data obtained by imaging behaviors of animals in real time.

The imaging device 10 may include a camera configured to capture a subject using, for example, a complementary metal-oxide semiconductor (CMOS) module, a charge coupled device (CCD) module, and the like. In this case, an input image frame is provided to the CMOS module or the CCD module in the imaging device 10 through a lens, and the CMOS module or the CCD module converts an optical signal of the subject passing through the lens into an electrical signal (image data) and outputs the result.

Meanwhile, the imaging device 10 according to the present embodiment has a network function and transmits the image data obtained by imaging animals to a first server 100. When the imaging device transmits the image data obtained by imaging animals to the first server 100, the captured image data may be transmitted in a predetermined period in order to minimize a load on a network or may be transmitted in real time in order to monitor more accurately.

The first server 100 may be a general-type server configured to provide predetermined information in response to an access request of a client, is connected to the imaging device 10 and the secondary system via a communication network, receives the image data from the imaging device 10, and transmits predetermined information to the secondary system.

In this case, the communication network may include a communication network using wired and/or wireless communication such as a TP, a coaxial cable, an optical fiber, micro waves, and RF, or a high-speed backbone network capable of providing high-capacity and long distance data services such as a general Internet network. In addition, the communication network may include a next generation wired network for providing all Internet protocol (ALL-IP)-based high speed services which mediates transmission and reception of signals and data between systems.

In particular, the first server 100 according to the present embodiment receives the image data from the imaging device 10 in order to detect whether animals managed in the barn are affected with an infectious disease, identifies an infectious-disease-suspicious sign in animals of the image data by analyzing the received data, and transmits a suspected symptom occurrence signal to the secondary system.

The secondary system includes a second server and the like, receives the suspected symptom occurrence signal from the primary system, analyzes image data on a subject suspected of having the infectious disease included in the received suspected symptom occurrence signal to re-diagnose occurrence of the infectious disease, and transmits a warning signal to a tertiary system side when it is determined that the infectious disease has occurred based on a re-diagnosis result. Meanwhile, the warning signal may have a form of a text message that is transmitted using LTE and 3G service networks.

The tertiary system is a terminal of a manager responsible for managing and preventing infectious diseases and may be implemented in various forms. Such a manager terminal may include a cellular phone, a smartphone, a laptop computer, a PC, personal digital assistants (PDAs), and the like.

The manager terminal receives the warning signal from the secondary system, requests a field image and surrounding environment information from the primary system and receives and displays the result to the manager, receives a final definite diagnosis analysis of infectious disease occurrence from the manager and issues an infectious disease occurrence alarm, and transmits the alarm to an infectious disease-related organization.

Figure 2:
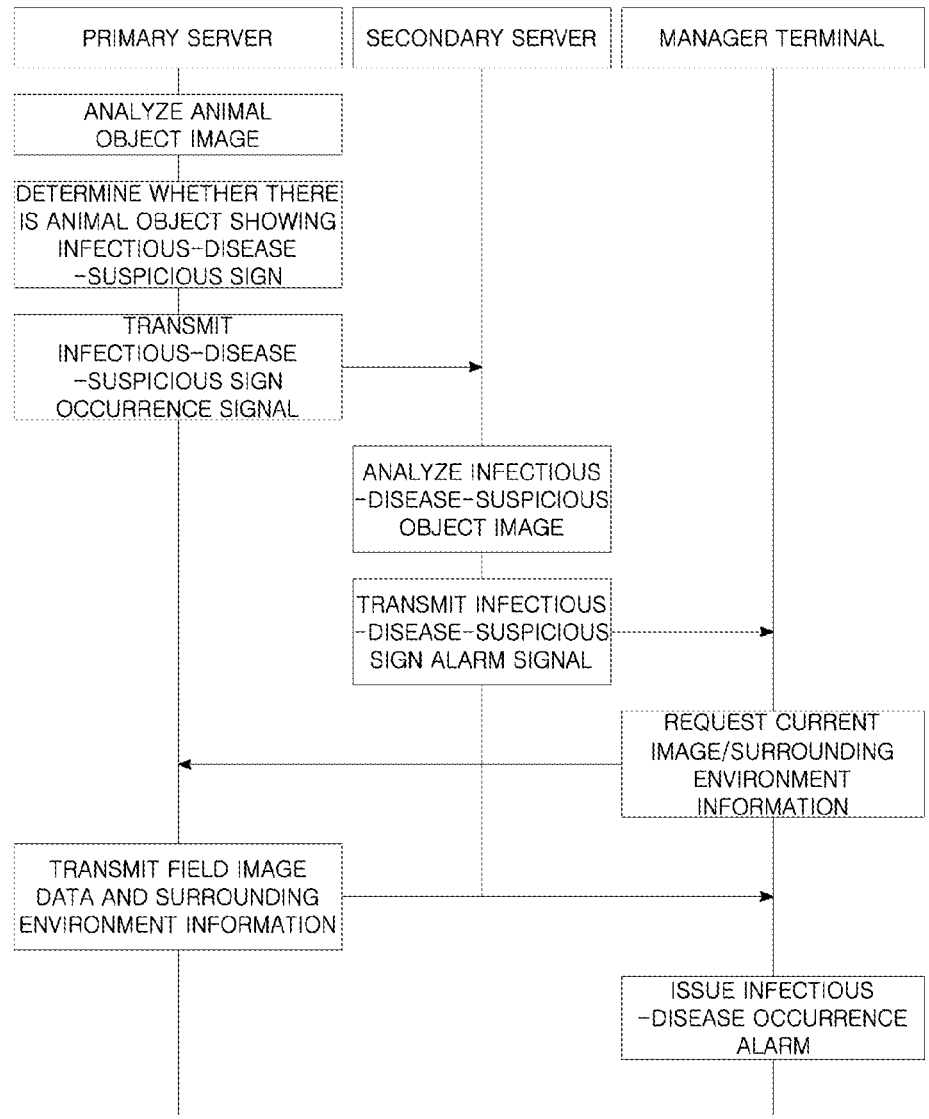
FIG. 2 is a sequence diagram illustrating the infectious disease monitoring system illustrated in FIG. 1.

FIG. 2 illustrates an infectious disease monitoring method of the infectious disease monitoring system according to the specific present embodiment.

As illustrated in FIG. 2, the first server located in the field in the barn receives first image data on the barn, analyzes an image of an animal subject, and determines whether there is an animal subject showing an infectious-disease-suspicious sign among animal subjects in the barn through image analysis. In addition, when there is at least one animal subject showing the symptoms suspected of having the infectious disease, the first server transmits a suspected symptom occurrence signal indicating that occurrence of the infectious disease is suspected in the barn to the external second server side. In this case, the first server may add the image data on a subject suspected of having the infectious disease to the suspected symptom occurrence signal.

When the suspected symptom occurrence signal is received from the first server, the second server analyzes the image data on the subject suspected of having the infectious disease included in the signal and transmits the warning signal to the manager terminal side.

More specifically, the second server performs high-performance analysis on the image data on the subject suspected of having the infectious disease and analyzes a similarity with an infectious disease. In this case, when the similarity is preferably 80% or more, the second server may determine that there is a risk of infectious disease occurrence. In addition, the second server may request additional image data on the field from the first server side as necessary.

Also, when the barn is located in a zone that is at risk from an area in which an infection disease has already occurred based on location information of the barn in which the first server is located, the second server may determine that there is a risk of infectious disease occurrence. Meanwhile, when the infectious disease is avian influenza (AI), a second server 200 may determine a degree of risk of infectious disease occurrence in further consideration of information on bird wintering grounds and migratory routes of birds.

When the warning signal is received from the second server, the manager terminal requests image data on the field and surrounding environment information from the first server side, receives the image data on the field and the surrounding environment information in response thereto from the first server, and displays the received data and information to the manager. Accordingly, the manager may analyze the object showing the symptoms suspected of having the infectious disease with the naked eye, and may definitively diagnose infectious disease occurrence in the barn in further consideration of the surrounding environment information of the barn.

When a definite diagnosis of infectious disease occurrence is received from the manager, the manager terminal issues an infectious disease occurrence alarm. In this case, the infectious disease occurrence alarm may be transmitted to a device of a predetermined infectious disease-related organization. For example, the infectious disease occurrence alarm may be transmitted to a server or a terminal of a related organization such as a disaster management division of a ministry of agriculture, food and rural affairs of a local government, a terminal of a barn owner, and the like.

Figure 3:
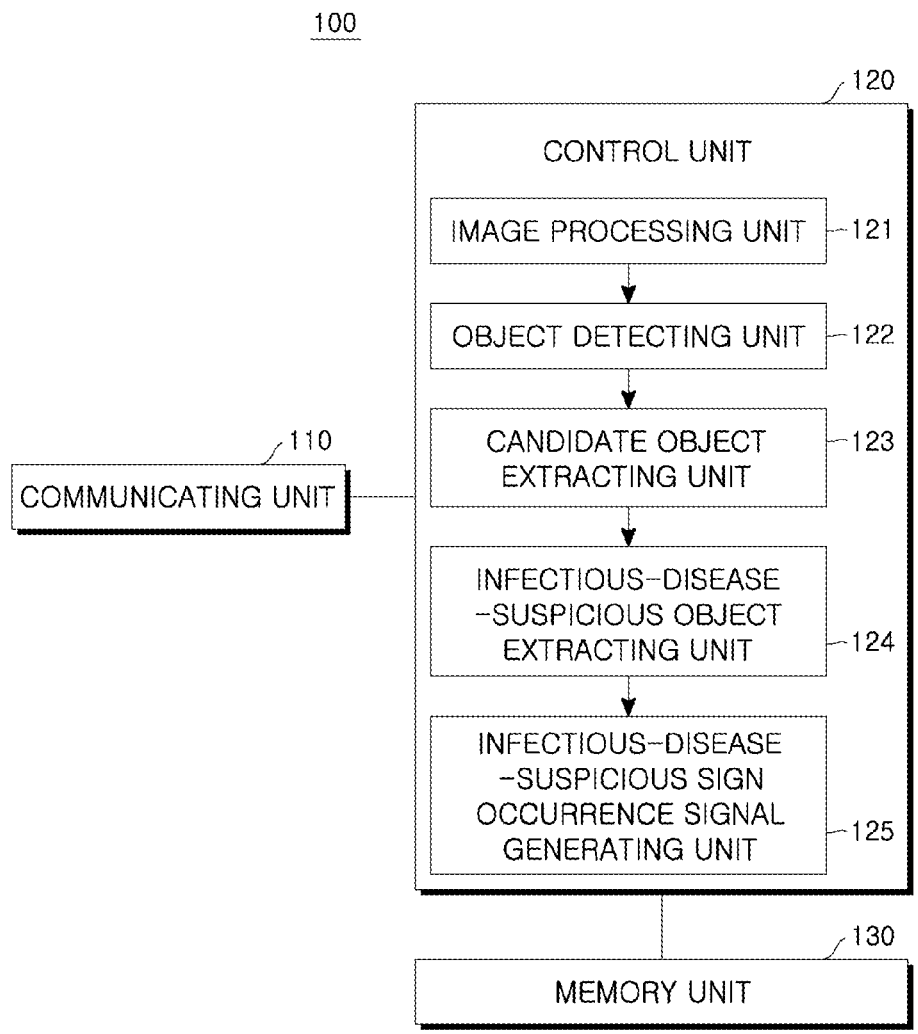
FIG. 3 is a control block diagram of a first server illustrated in FIG. 1.

FIG. 3 is a control block diagram of the first server illustrated in FIG. 1.

As illustrated in FIG. 3, the first server 100 according to the present embodiment includes a communicating unit 110, a control unit 120, and a memory unit 130. Meanwhile, all components of the first server illustrated in FIG. 3 are not essential components. A field server may be implemented by a greater number of components than the components illustrated or the first server may be implemented by a smaller number of components than the components illustrated. Hereinafter, the above-described components will be described in detail.

The communicating unit 110 includes at least one component configured to perform wired and/or wireless communication with the imaging device and the second server.

More specifically, the communicating unit 110 receives image data on animals in the barn from the imaging device and transmits the received data to the control unit 120. In addition, the communicating unit 110 transmits the suspected symptom occurrence signal indicating that there is an object showing the symptoms suspected of having the infectious disease in the barn to the second server serving as an external management server. Also, the communicating unit 110 may transmit additional field image data according to a request from the second server.

The control unit 120 controls overall operations of the first server 100.

In particular, the control unit 120 of the present embodiment includes an image processing unit 121, an object detecting unit 122, a candidate subject extracting unit 123, a subject suspected of having the infectious disease extracting unit 124, and a suspected symptom occurrence signal generating unit 125, and determines whether there is an animal subject suspected of having an infectious disease among animal subjects in the image data on an interior of the barn received from the communicating unit 110, and transmits a signal indicating suspicion when occurrence of the infectious disease is suspected.

The image processing unit 121 performs an image quality enhancement on the image data received from the communicating unit 110 and transmits the result to the object detecting unit 122.

The image processing unit 121 decreases noise in the image data and may perform image signal processing for image quality enhancement methods such as gamma correction, color filter array interpolation, color matrix, color correction, and color enhancement. The image processing unit 121 may also perform color processing, blur processing, edge enhancement processing, image analysis processing, image recognition processing, image effect processing, and the like.

The object detecting unit 122 detects at least one animal subject from the image data on which image signal processing has been performed by the image processing unit 121.

More specifically, the object detecting unit 122 detects an outline of the object in the image data, compares the detected outline with an appearance of the animal subject that is previously stored in the memory unit 130, and detects an object having an outline matching the appearance of the pre-stored animal subject as the animal subject. In this case, the appearance of the animal subject stored in the memory unit 130 may be at least one appearance of the animal subject. As described above, the object detecting unit 122 may detect an object having the matching outline as the animal subject, and at the same time, determine a type of the animal subject.

Also, the object detecting unit 122 extracts feature points of the object in the image data. When the extracted feature points match feature points of the animal subject that is previously stored in the memory unit 130 within proximity of a threshold value or more, the object detecting unit 122 may detect the object in the image data as the animal subject. In this case, the object detecting unit 122 may use a scale invariant feature transform (SIFT) or speeded up robust features (SURF) algorithm that extracts feature points from images of two objects to be compared and matches feature point descriptors of extracted two objects.

In addition, the object detecting unit 122 may detect the animal subject based on contours of objects in the image data. More specifically, the object detecting unit 122 detects contours of objects in the image data to generate an edge image, detects a contour from complete image data that is a background image of the barn stored in the memory unit 130 in advance to generate a background edge image, and may detect the animal subject in a difference image obtained by subtracting the background edge image from the edge image.

In this case, the object detecting unit 122 uses gradient information of an image data frame, detects a contour of the object present in the frame as an edge and generates an edge image. Here, the gradient information is a value generated from a difference value between adjacent pixels among predetermined pixels in the frame and refers to a sum of absolute difference values. The edge refers to a boundary between objects using the gradient information.

Also, the object detecting unit 122 detects an edge of an object corresponding to a background in a pre-imaged complete image data frame of the inside of the barn and generates a background edge image. The background edge image in this case may be an image in which contours of objects in a predetermined area are detected as a background edge, or an image in which a plurality of pre-imaged complete image data frames of the inside of the barn are compared and a contour of an object that is repeatedly shown identically a predetermined number of times or more is detected as a background edge.

In addition, the object detecting unit 122 may detect an animal subject in the image data using an object detection classifier. In this case, the object detection classifier is obtained by learning and building a training DB from animal subject images that are previously imaged while postures or external environments of the animal subject are changed. Such an object detection classifier generates a DB of the animal subject using various learning algorithms such as a support vector machine (SVM), neural networks, and an AdaBoost algorithm. Specifically, the object detecting unit 122 detects an edge of an object corresponding to a foreground in a pre-imaged image data frame of the background of the inside of the barn, applies the detected edge of the foreground object to the image data, and applies the object detection classifier to an area of the image data to which the edge of the foreground object is applied to quickly detect the animal subject.

The candidate subject extracting unit 123 tracks at least one animal subject detected by the object detecting unit 122 and extracts an animal subject showing a predetermined behavior pattern related to the infectious disease as a candidate subject.

The candidate subject extracting unit 123 assigns ID information to each animal subject and stores position coordinate values in the image data frame of the animal subject to which the ID information is assigned in the memory unit 130 in association with the ID information. In addition, the candidate subject extracting unit 123 may calculate a time the animal subject spends at the same position and store the time in the memory unit 130 in association with the ID information.

Figure 4:
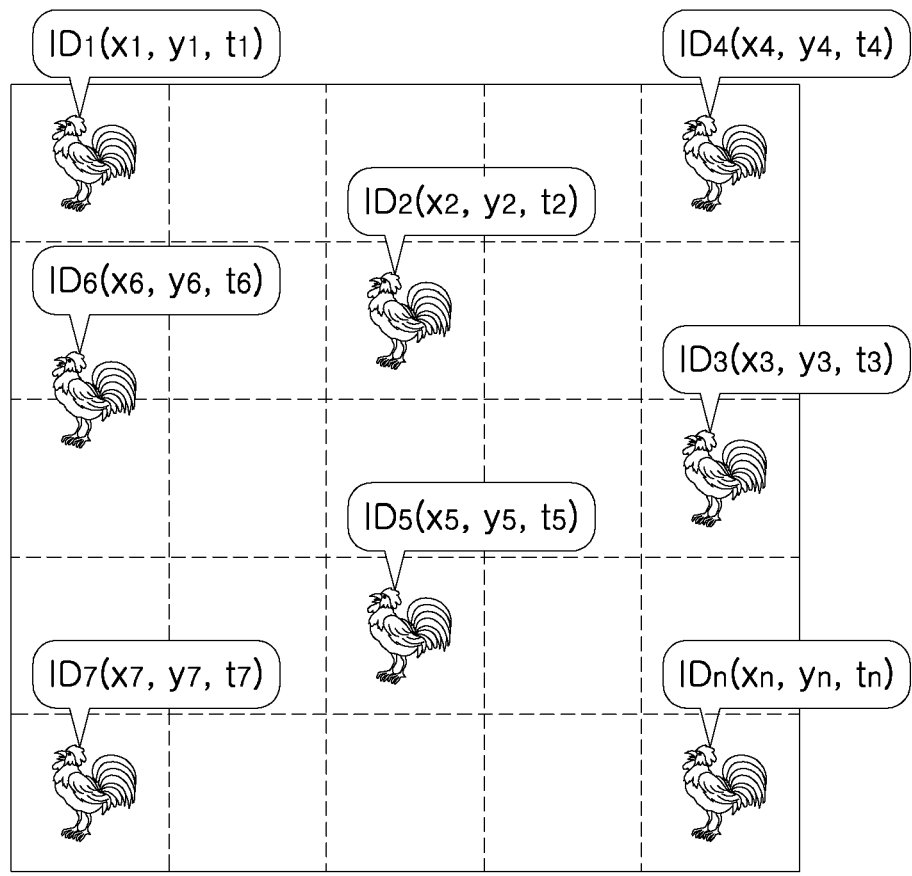
FIG. 4 is a diagram illustrating a frame of image data obtained by assigning an ID to each animal subject in a candidate subject extracting unit of the first server illustrated in FIG. 3.

FIG. 4 illustrates an example in which the ID and position and time information of each animal subject in the image data frame are stored by the candidate subject extracting unit 123. As illustrated in FIG. 4, it may be seen that a current position of an animal subject having $ID_1$ in real time image data is $(x_1', y_1')$ and a time spent at the position is currently $t_1'$. While the ID and the position and time information are displayed together in FIG. 4, only the ID may be displayed, only the ID and location information may be displayed, or only a predetermined marking may be displayed on each object.

Also, when the animal subject moves, the candidate subject extracting unit 123 updates position coordinate values of the animal subject that has moved in the ID information and stores a history of the position coordinate and time information of the animal subject in association with the ID information of the animal subject. Therefore, the candidate subject extracting unit 123 may track a moving history and a behavior pattern of the animal subject using history information of the position coordinate and time information of the animal subject.

The candidate subject extracting unit 123 selects a specific infectious disease from among infectious diseases of the animal subject and extracts an animal subject showing a specific behavior pattern as a sign of the selected specific infectious disease. For example, when the animal subject is poultry, the candidate subject extracting unit 123 may extract an animal subject having a behavior pattern (birds extend their wings and are gathered together) or a behavior pattern having a small amount of activity (birds move slowly or crouch), which is a sign of AI, as a candidate subject.

Figure 5A:
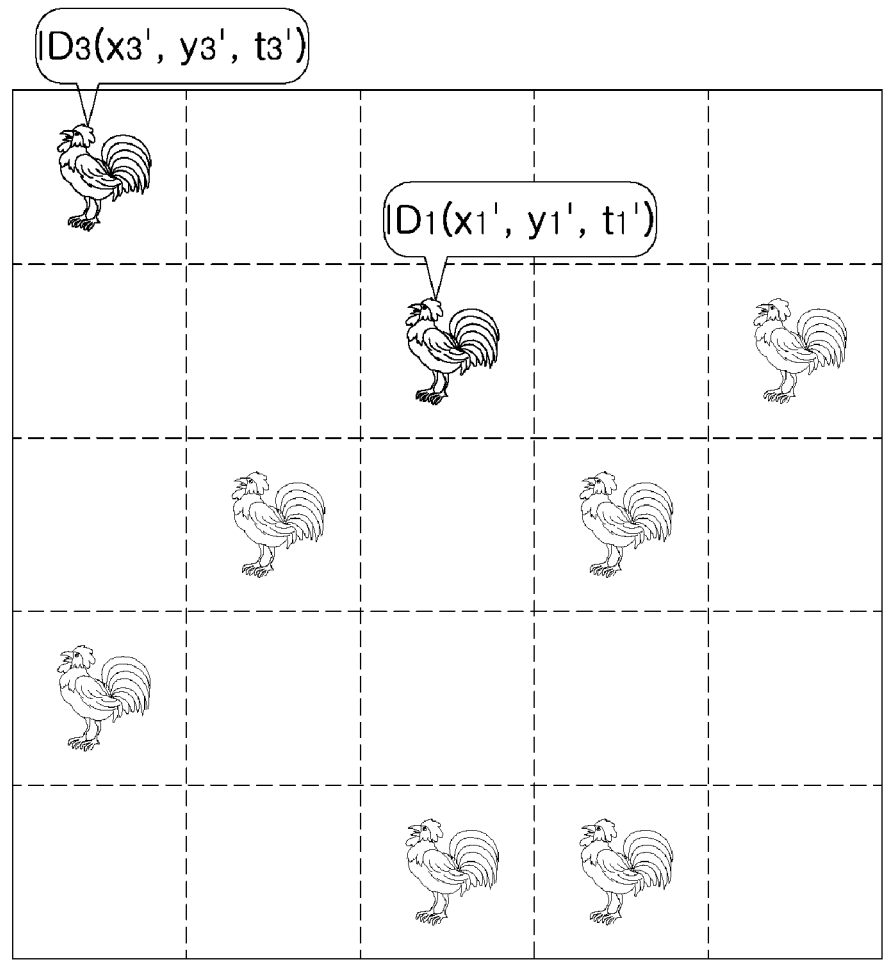
FIG. 5A is a diagram illustrating a frame of image data obtained by extracting a candidate subject in the candidate subject extracting unit of the first server illustrated in FIG. 3.

The candidate subject extracting unit 123 calculates an amount of activity during a specific time period for each ID. When the calculated amount of activity is a reference value or less, the candidate subject extracting unit 123 extracts an animal subject having the ID as a candidate subject. For example, in the case of poultry, in order to detect an object having a small amount of activity which is a sign of AI, a time period in which birds are generally active is set as a specific time period, and an object having an amount of activity equal to or less than a reference value during the specific time period may be extracted as a candidate subject. The candidate subject extracted in this manner may be displayed ($ID_1$, $ID_3$, and $ID_N$) distinguishably from a normal animal subject in real time image data as illustrated in FIG. 5A, and the distinguishably displayed candidate subject ($ID_1$, $ID_3$, and $ID_N$) may be a target for which correspondence to the subject suspected of having the infectious disease will be determined later.

Also, the candidate subject extracting unit 123 may calculate an amount of activity based on the stored moving history of the animal subject during a specific time period.

More specifically, the candidate subject extracting unit 123 may calculate the amount of activity by calculating a total moving distance based on position coordinate values that are stored in the moving history during a specific time period of the animal subject. Therefore, an animal subject having a total moving distance smaller than the reference value may be extracted as a candidate subject having a small amount of activity.

Figure 5B:
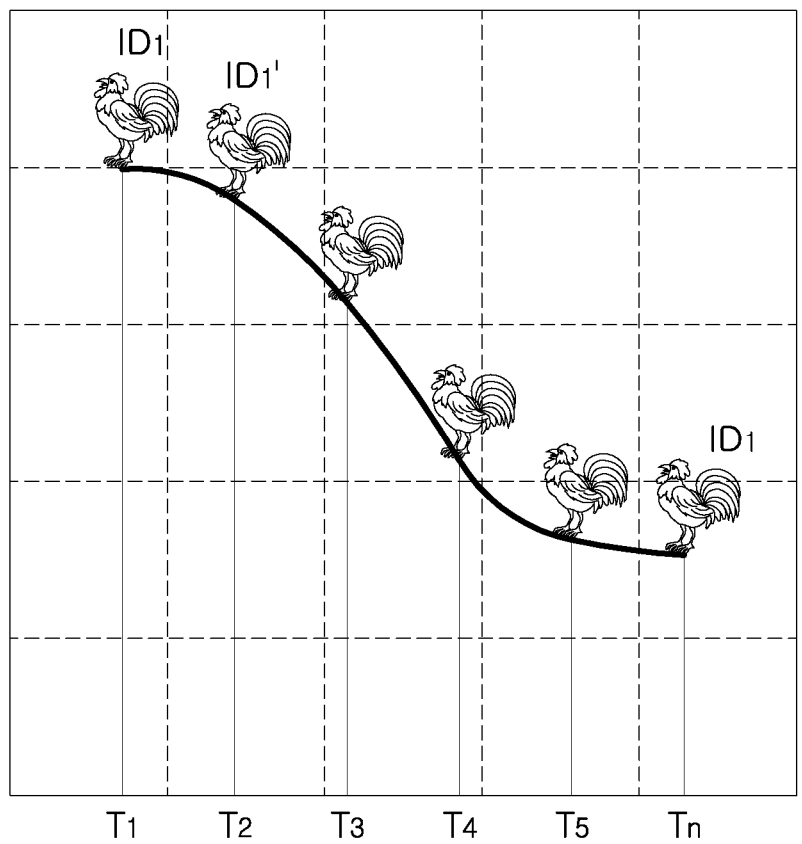
FIG. 5B is a diagram illustrating a process of extracting a candidate subject in the candidate subject extracting unit of the first server illustrated in FIG. 3.
Figure 5C:
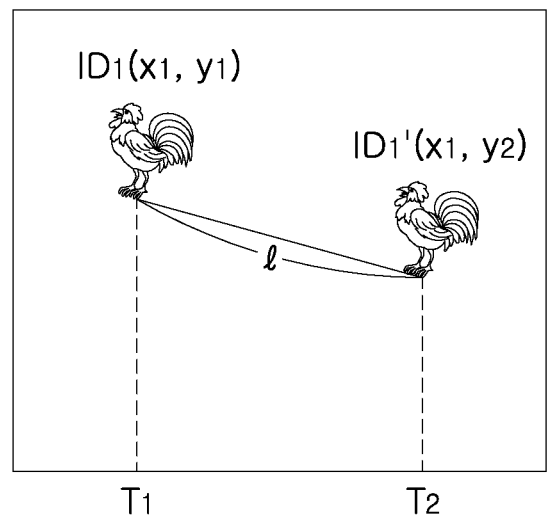
FIG. 5C is a diagram illustrating a process of extracting a candidate subject in the candidate subject extracting unit of the first server illustrated in FIG. 3.

For example, as illustrated in FIG. 5B, when an animal subject of $ID_1$ moves during a specific time period of $T_1$ to $T_n$, the candidate subject extracting unit 123 may calculate a total moving distance using a history of changes in position coordinates during $T_1$ to $T_n$. In this case, the specific time period ($T_1$ to $T_n$) is divided into predetermined time intervals ($T_1$ to $T_2$, $T_2$ to $T_3$, $T_3$ to $T_4$, $T_4$ to $T_5$, and $T_5$ to $T_n$), a straight line moving distance is calculated for each time interval, and a sum of the calculated values may be calculated as a total moving distance. Meanwhile, for example, a straight line moving distance during a first time interval of $T_1$ to $T_2$ may be calculated as a straight line distance (l) from position coordinates ($x_1$ and $y_1$) of an animal subject ($ID_1$) at $T_1$ to position coordinates ($x_2$ and $y_2$) of the animal subject ($ID_1'$) at $T_2$ as illustrated in FIG. 5C.

Also, the candidate subject extracting unit 123 may calculate an amount of activity based on a time the animal subject spends at the same position for a specific time period. The candidate subject extracting unit 123 calculates the largest value among times spent by birds at the same positions stored in the moving history during a specific time period, calculates a value inversely proportional to the calculated largest value as the amount of activity, and may extract an animal subject that spends a long time at one place as a candidate subject having a small amount of activity.

The subject suspected of having the infectious disease extracting unit 124 compares image data on the candidate subject extracted by the candidate subject extracting unit 123 with at least one external lesion related to the infectious disease, determines whether an appearance of the candidate subject matches the external lesion, and extracts the matching candidate subject as the subject suspected of having the infectious disease. For example, in the case of poultry, the external lesion of AI may be cyanosis of a chicken comb and a leg part. In this case, the subject suspected of having the infectious disease extracting unit 124 processes image data on the chicken comb and the leg part of the candidate subject based on an HSI color model. When the processed image data on the chicken comb and the leg part matches the external lesion of cyanosis with a similarity of a predetermined value or more, the subject suspected of having the infectious disease extracting unit 124 extracts the candidate subject as the subject suspected of having the infectious disease.

Meanwhile, the subject suspected of having the infectious disease extracting unit 124 detects an end (body end) that is a target for determining the external lesion in the image data on the candidate subject based on a database of end positions for each posture of the animal subject stored in the memory unit 130, and may determine whether an appearance of the detected end matches the external lesion.

In this case, a database of end positions for each posture is a database in which each body end of the animal subject posing a specific posture, for example, positions of a head and feet, is learned and stored for each posture. Such a database of end positions for each posture is generated such that a skeletonization or thinning algorithm is applied to image data on the animal subject posing a specific posture, a central axis of the animal subject is extracted, and each end of the extracted central axis is learned as a position of a body end of the animal subject posing the specific posture. For example, in the case of poultry, in the database of end positions for each posture, position information on ends such as a head, wing, and feet of the poultry is learned from postures in which poultry may pose such as crouching postures, standing postures, and wing-extending postures.

Figure 6:
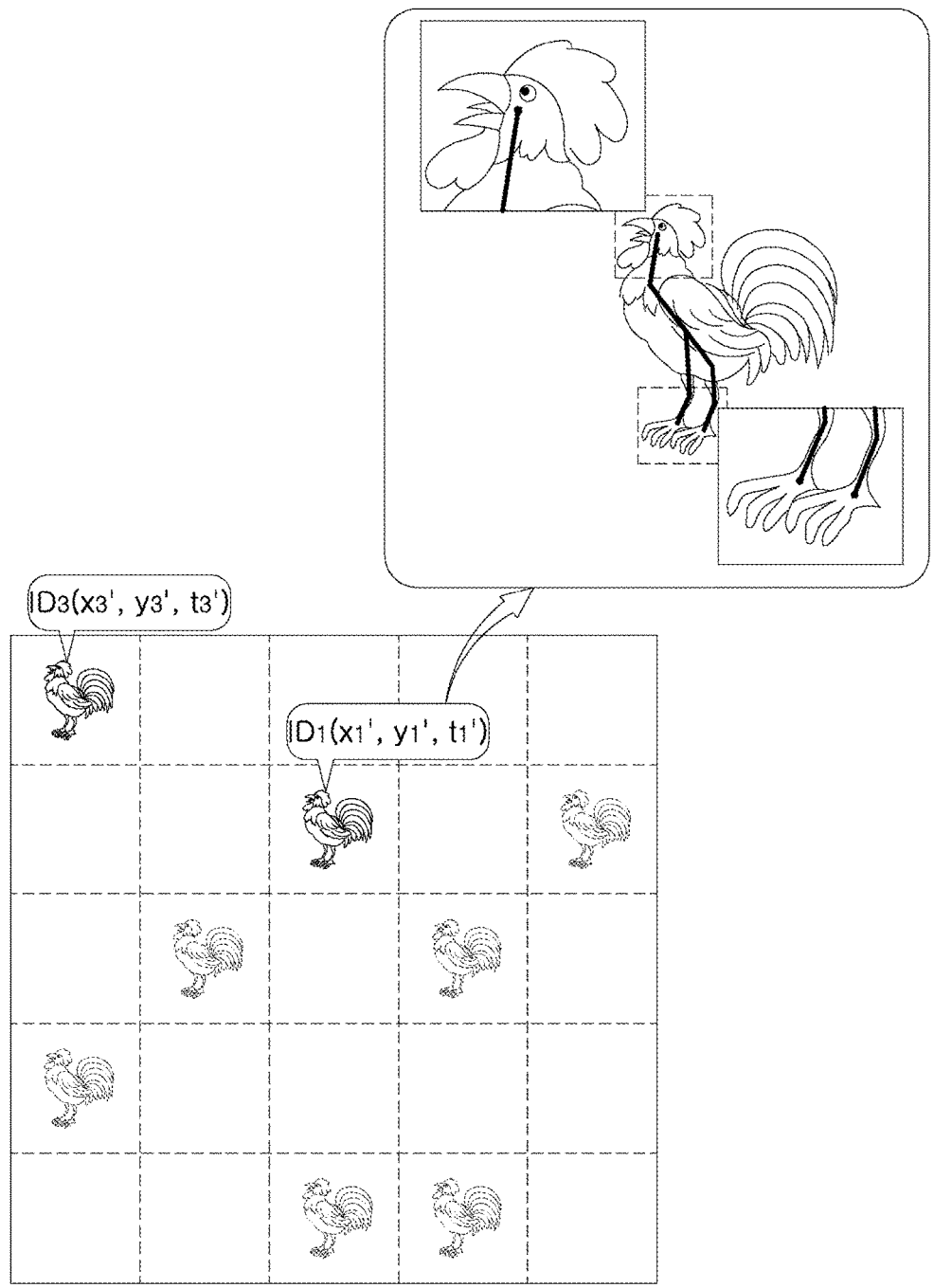
FIG. 6 is a diagram illustrating a process of extracting a subject suspected of having the infectious disease in a subject suspected of having the infectious disease extracting unit of the first server illustrated in FIG. 3.

As illustrated in FIG. 6, for example, the subject suspected of having the infectious disease extracting unit 124 determines whether the external lesion occurs by searching specific posture matching image data on a candidate subject ($ID_1$) and a central axis and each end position according to the specific posture in the database of end positions for each posture, and performing image processing such as enlarging and coloring the image data on the end (a head part and a leg part in FIG. 6) in which the external lesion of the infectious disease is located.

When the subject suspected of having the infectious disease is extracted by the subject suspected of having the infectious disease extracting unit 124, the suspected symptom occurrence signal generating unit 125 generates a suspected symptom occurrence signal indicating that the subject suspected of having the infectious disease is extracted in the barn. In this case, the suspected symptom occurrence signal may include the image data on the extracted subject suspected of having the infectious disease.

Figure 7:
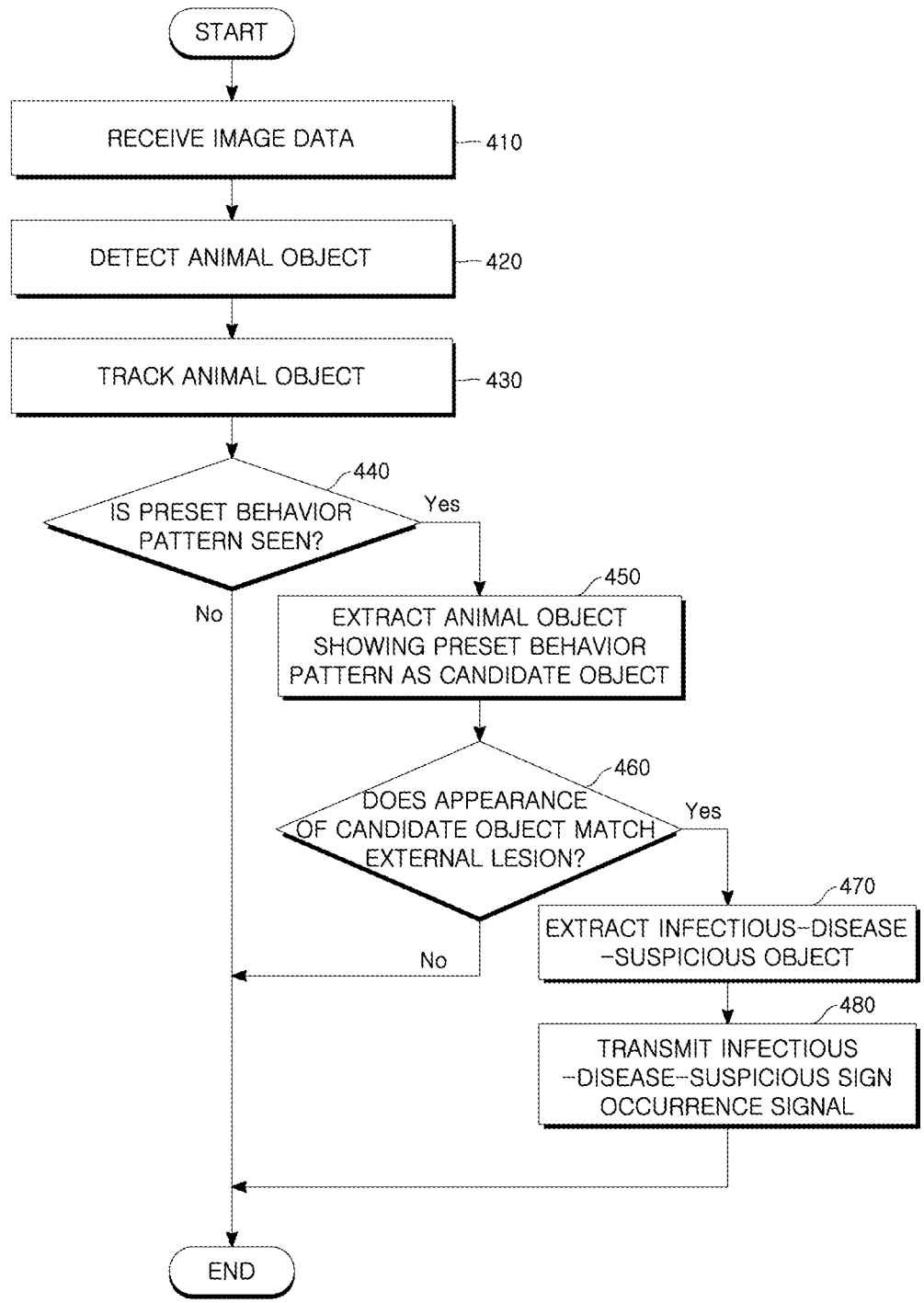
FIG. 7 is a flowchart illustrating a process of finding an infectious-disease-suspicious sign in a control unit of the first server illustrated in FIG. 1.

FIG. 7 is a flowchart illustrating a process of finding an symptoms suspected of having the infectious disease in the control unit of the first server illustrated in FIG. 3.

As illustrated in FIG. 7, first, the control unit receives the image data on the animal in the barn from the imaging device (410). In this case, image processing for image quality enhancement may be performed on the image data.

In addition, the control unit detects at least one animal subject in the received image data (420), and tracks the detected animal subject (430). In this case, a predetermined ID is assigned to each detected animal subject in order to track the animal subject, and a moving history in which position coordinate and time information of the animal subject in association with the assigned ID is stored may be stored.

Also, the control unit extracts an animal subject showing a predetermined behavior pattern among animal subjects as a candidate subject (440 and 450). That is, the control unit determines whether there is an animal subject having a behavior pattern related to a lesion of a specific infectious disease (440), and extracts the animal subject as a candidate subject (450). For example, when the specific infectious disease is AI, an object showing a behavior pattern (birds have a small amount of activity or are gathered together while extending their wings) may be extracted as a candidate subject.

Meanwhile, the control unit may calculate an amount of activity of the animal subject during a specific time and extract an animal subject having the calculated amount of activity less than the reference value as a candidate subject. In this case, the amount of activity may be calculated in consideration of a change history of position coordinates during a specific time, a time history of spending time at the same position, and the like. The specific time may be set as a predetermined time range in which the animal shows relatively active movement.

Also, the control unit determines whether image data on the extracted candidate subject matches the external lesion related to the infectious disease and extracts a candidate subject having the external lesion as a subject suspected of having the infectious disease (460 and 470). When the infectious disease is, for example, AI, the control unit may determine whether cyanosis has occurred in a chicken comb and a leg part in the image data on the candidate subject.

Also, when the subject suspected of having the infectious disease is extracted (470), the control unit transmits a suspected symptom occurrence signal indicating that there is an object having a symptoms suspected of having the infectious disease in the barn (480). In this case, the suspected symptom occurrence signal may include the image data on the subject suspected of having the infectious disease or field image data.

Figure 8:
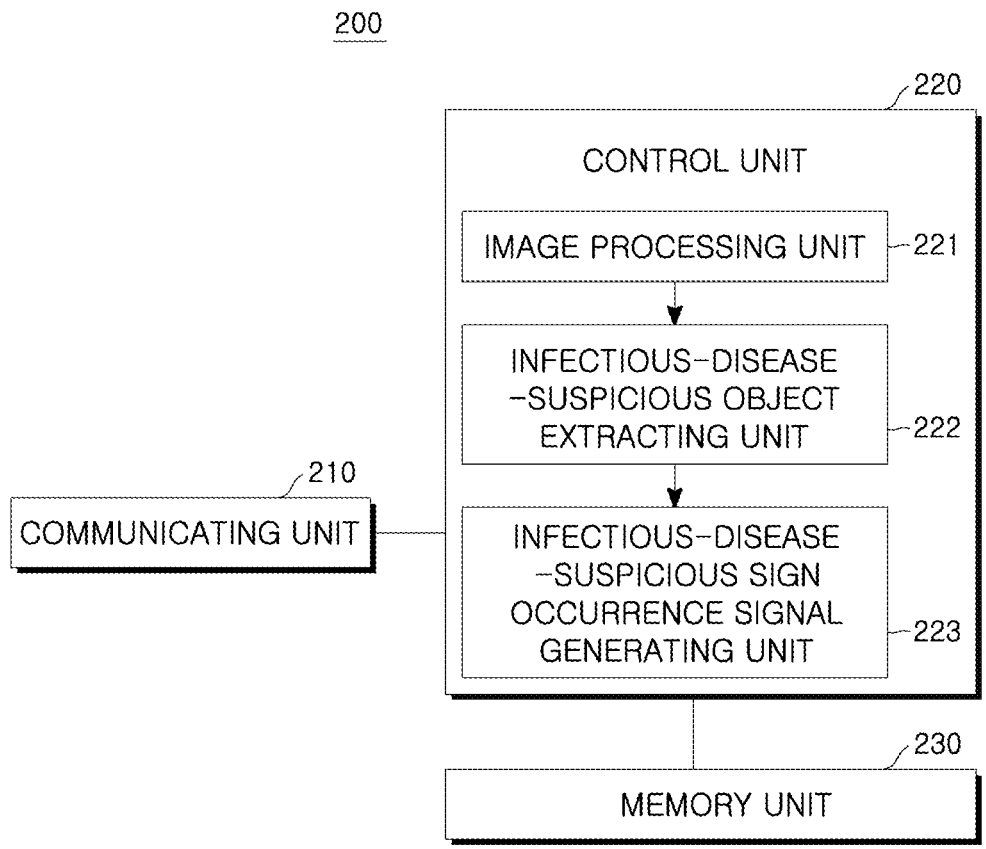
FIG. 8 is a control block diagram of a second server illustrated in FIG. 1.

FIG. 8 is a control block diagram of the second server illustrated in FIG. 1.

As illustrated in FIG. 8, the second server 200 according to the present embodiment includes a communicating unit 210, a control unit 220, and a memory unit 230. Meanwhile, all components of the second server illustrated in FIG. 8 are not essential components. The second server may be implemented by a greater number of components than the components illustrated, or the second server may be implemented by a smaller number of components than the components illustrated. Hereinafter, the above-described components will be described in detail.

The communicating unit 210 includes at least one component configured to perform communication with the first server and the manager terminal.

More specifically, the communicating unit 210 receives the suspected symptom occurrence signal from the first server side. In this case, the suspected symptom occurrence signal may include the image data on the subject suspected of having the infectious disease or image data on the inside of the field of the image. Also, the communicating unit 210 may transmit a control signal for requesting an additional image from the first server side under control of the control unit 220.

Also, the communicating unit 210 may request additional information for infectious disease diagnosis from an external database and receive the result. For example, the communicating unit may receive information on migratory bird entry routes and AI-confirmed areas for AI diagnosis.

Also, the communicating unit 210 transmits the warning signal to the manager terminal side.

The control unit 220 controls overall operations of the second server.

In particular, the control unit 220 of the present embodiment includes an image analyzing unit 221, an infectious disease determining unit 222, and a warning signal generating unit 223.

The image analyzing unit 221 performs predetermined image processing on the image data on the subject suspected of having the infectious disease received by the communicating unit 210, and performs a sophisticated analysis on the subject suspected of having the infectious disease in the image data.

The infectious disease determining unit 222 determines that there is a risk of the infectious disease when a similarity with the infectious disease is a predetermined value or more based on the analysis result of the image analyzing unit 221, and transmits a signal to the warning signal generating unit 223.

Also, the infectious disease determining unit 222 determines a risk of infectious disease occurrence in further consideration of additional information received from the external database in addition to image analysis by the image analyzing unit 221.

When the barn is located in a zone that is at risk from an area in which an infectious disease has already occurred based on infectious disease definite diagnosis area information, the infectious disease determining unit 222 may determine that there is a high risk of infectious disease occurrence. Also, when the infectious disease is AI, the infectious disease determining unit 222 may determine a degree of risk of infectious disease occurrence in further consideration of migratory bird entering paths.

When the signal is received from the infectious disease determining unit 222, the warning signal generating unit 223 generates a warning signal. In this case, the warning signal has a form of a text message.

Figure 9:
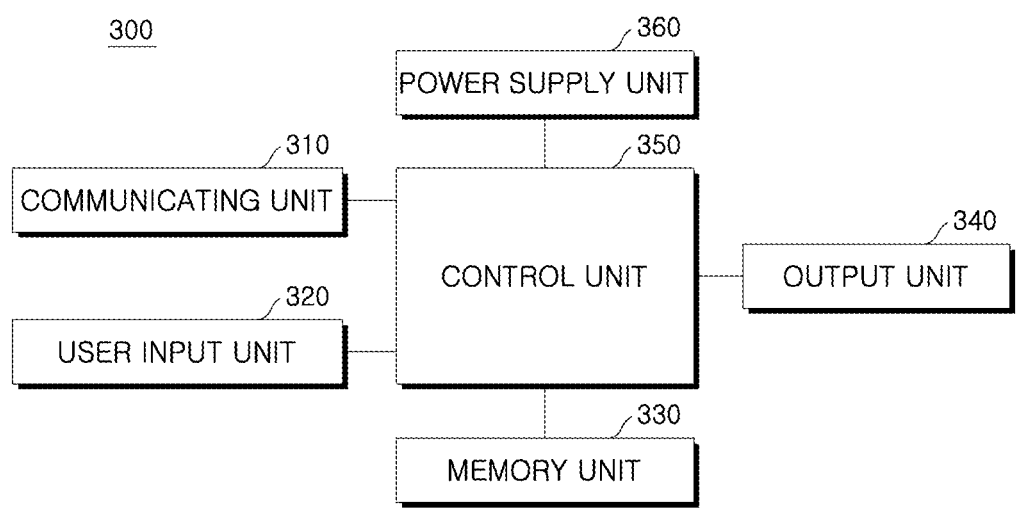
FIG. 9 is a control block diagram of a manager terminal illustrated in FIG. 1.

FIG. 9 is a control block diagram of a manager terminal illustrated in FIG. 1.

As illustrated in FIG. 9, a manager terminal 300 includes a communicating unit 310, a user input unit 320, a memory unit 330, an output unit 340, a control unit 350, and a power supply unit 360. Meanwhile, all components of the manager terminal illustrated in FIG. 9 are not essential components. The manager terminal may be implemented by a greater number of components than the components illustrated or the manager terminal may be implemented by a smaller number of components than the components illustrated. Hereinafter, the above-described components will be described in detail.

The communicating unit 310 includes a communicating module configured to perform communication with the second server, the first server, and the like.

Specifically, the communicating unit 310 receives a warning signal indicating a risk of infectious disease occurrence from the second server. In this case, the warning signal has a form of a text message.

In addition, the communicating unit 310 may request a field image and surrounding environment information from the first server side under control of the control unit 350 and receive the result.

Also, the communicating unit 310 may transmit the infectious disease occurrence alarm signal to an infectious disease-related organization such as a disaster management division of a ministry of agriculture, food and rural affairs of a local government or the barn.

The user input unit 320 generates input data for operational control of the terminal 300. The user input unit 320 may be a key pad, a dome switch, a touch pad, a jog wheel, a jog switch, and the like. In particular, when the touch pad forms a cross-layer structure with the output unit 340 to be described, this may be called a touch screen. The user input unit 320 may receive a definite diagnosis of infectious disease occurrence from the manager.

The output unit 340 displays and outputs information processed by the manager terminal.

Meanwhile, when the output unit 340 and the touch pad form a cross-layer structure and the touch screen is formed, the output unit 340 may be used as an input device in addition to the output device. The output unit 340 may include at least one among a liquid crystal display, a thin-film transistor liquid crystal display, an organic light-emitting diode, a flexible display, and a 3D display. The output unit 340 displays the image data on the animal that is a field image and surrounding environment information received by the communicating unit 310, and allows the manager to determine whether the animal subject shows the symptoms suspected of having the infectious disease with the naked eye, and definitely diagnose whether the infectious disease has occurred in the barn through the surrounding environment information in the barn.

The control unit 350 controls overall operations of the manager terminal. When the warning signal is received from the communicating unit 310, the control unit 350 performs a control such that a signal requesting field image data and surrounding environment information from the first server side is transmitted through the communicating unit 310.

Also, the control unit 350 stores the received animal image data and surrounding environment information in the memory unit 330 and displays the information through the output unit 340. Also, when a definite diagnosis of infectious disease occurrence is received through the user input unit 320, the control unit 350 performs a control such that an alarm signal indicating the diagnosis is transmitted to the predetermined infectious disease-related organization, the barn, and the like.

The power supply unit 360 receives external power and internal power under control of the control unit 350 and supplies power necessary for operations of each component.

According to the aspect of the present invention, it is possible to build a system in which space conditions of the barn are understood in real time based on real time image information obtained by the imaging device installed in the barn, situations in which the infectious disease may occur are predicted and recognized, and information may be provided to a barn manager and related organizations such as officials of a ministry of agriculture, food and rural affairs, national centers for disease control and prevention, and a ministry of environment. Accordingly, it is possible to ultimately decrease national financial losses and damages of farms.

Technology for monitoring the infectious disease based on real time image data on animals in the barn in this way may be implemented in an application or a form of a program instruction that may be executed through various program components, and may be recorded in computer readable recording media. The computer readable recording media may include a program instruction, a data file, a data structure, and the like, or combinations thereof.

The program instruction recorded in the computer readable recording media may be specially designed and prepared for the invention or may be an available well-known instruction for those skilled in the field of computer software.

Examples of the computer readable recording media include, for example, magnetic media such as a hard disk, a floppy disk, and a magnetic tape, optical media such as a CD-ROM and a DVD, magneto-optical media such as a floptical disk, and a hardware device, such as a ROM, a RAM, and a flash memory, that is specially configured to store and perform the program instruction.

Examples of the program instruction may include a machine code generated by a compiler and a high-level language code that can be executed in a computer using an interpreter. Such a hardware device may be configured as at least one software module in order to perform operations of the invention and vice versa.

According to the aspect of the present invention, it is possible to build a system in which space conditions of the barn are understood in real time based on real time image information obtained by the imaging device installed in the barn, situations in which the infectious disease may occur are predicted and recognized, and information may be provided to a barn manager and related organizations such as officials of a ministry of agriculture, food and rural affairs, national centers for disease control and prevention, and a ministry of environment.

While the present invention have been described above with reference to the embodiments, it may be understood by those skilled in the art that various modifications and alternations may be may be made without departing from the spirit and scope of the present invention described in the appended claims.

What is claimed is:

1. An infectious disease monitoring system comprising:
an imaging device capturing and transmitting image data on animals managed in a barn;
a first server comprising an animal image detecting unit detecting at least one animal object from the image data, and determining whether an animal suspected of having an infectious disease is detected from the image data received from the imaging device, and, when the animal suspected of having the infectious disease is detected, transmitting a suspected symptom occurrence signal along with the image data of the subject suspected of having the infectious disease, wherein the animal image detecting unit compares an outline of objects in the image data with pre-stored data to detect the at least one animal object;
wherein the first server comprises:
a candidate object extracting unit tracking the at least one animal object, and extracting at least one candidate animal object having a predetermined behavior pattern of the infectious disease among the at least one animal object;
an animal suspected of having the infectious disease extracting unit determining whether the image data of an outward appearance of the at least one candidate object is matched with an external lesion of the infectious disease and extracting the animal suspected of having the infectious disease from the at least one candidate animal object; and
a suspected symptom occurrence signal generating unit generating the suspected symptom occurrence signal including the image data on the animal suspected of having the infectious disease when the animal suspected of having the infectious disease is extracted;

a second server confirming an occurrence of the infectious disease by analyzing the image data of the animal suspected of having the infectious disease upon receipt of the suspected symptom occurrence signal from the first server, and transmitting a warning signal when confirmed the occurrence of the infectious disease; and a manager terminal requesting the image data of the animals from the first server upon receipt of the warning signal from the second server and displaying the image data of the animals, wherein the animal image detecting unit generates an edge image using contours of objects in the image data, generates a background edge image using a pre-stored background image of the barn, subtracts the background edge image from the edge image to make a difference image, identifies the at least one animal object by using a scale invariant feature transform (SIFT) or speeded up robust features (SURF) algorithm that extracts feature points from the image data, and detects the at least one animal object using an object detection classifier, wherein the object detection classifier generates a database (DB) for the at least one animal object using at least one of a support vector machine (SVM), neural networks, and an AdaBoost algorithm.

2. The infectious disease monitoring system of claim 1, wherein the candidate object extracting unit calculates an amount of activity of the at least one animal object during a specific time period, and extracts the at least one candidate object having the amount of activity equal to or less than a reference value.

3. The infectious disease monitoring system of claim 2, wherein the candidate object extracting unit calculates the amount of activity by calculating a total moving distance based on position coordinate values that are stored in a moving history during a specific time period of the animal object, and the animal object having a total moving distance smaller than a reference value is extracted as a candidate object having a small amount of activity.

4. The infectious disease monitoring system of claim 1, wherein the second server transmits the warning signal when a similarity of the image data of the object suspected of having the infectious disease with the infectious disease is the same or higher than a predetermined value.

5. The infectious disease monitoring system of claim 1, wherein the second server transmits the warning signal with a consideration of location information of the barn in which the animal suspected of having the infectious disease is extracted.

6. The infectious disease monitoring system of claim 5, wherein the second server transmits the warning signal when the barn in which the animal suspected of having the infectious disease is extracted is located in a predetermined danger radius from an area in which the infectious disease is reported.

7. The infectious disease monitoring system of claim 1, wherein the manager terminal transmits an infectious disease occurrence alarm to a device of a predetermined infectious disease related organization upon receipt of a confirmation of the infectious disease occurrence based on the displayed image data on the animals from the manager.

8. The infectious disease monitoring system of claim 1, wherein the animal image detecting unit extracts feature points of the at least one animal object from the image data, and when the extracted feature points of the at least one animal object is within proximity of a predetermined value from pre-stored data, the animal image detecting unit determines the at least one animal object as an animal.

9. The infectious disease monitoring system of claim 1, wherein the candidate object extracting unit assigns ID information to each of the at least one animal object and stores respective position coordinate values in the image data frame thereof, and wherein the candidate object extracting unit calculates an amount of activity of the at least one animal object based on the largest value among times spent by the at least one animal object at the same positions for a predetermined period of time and uses a value inversely proportional to the largest value as the amount of activity of the at least one animal object.

10. The infectious disease monitoring system of claim 1, wherein when the animal object moves, the candidate object extracting unit updates the position coordinate values of the animal object and stores a history of the position coordinate and time information of the animal object in association with the ID information.

11. A method for infectious disease monitoring of animals managed in a barn, the method comprising:

capturing and transmitting image data on the animals managed in the barn;

detecting, at an animal image detecting unit of a first server, at least one animal object from the image data and determining whether an animal suspected of having an infectious disease is detected from the image data received from the imaging device, and, when the animal suspected of having the infectious disease is detected, transmitting a suspected symptom occurrence signal along with the image data of the subject suspected of having the infectious disease, wherein the animal image detecting unit compares an outline of objects in the image data with pre-stored data to detect the at least one animal object;

wherein the first server comprises:

a candidate object extracting unit tracking the at least one animal object, and extracting at least one candidate animal object having a predetermined behavior pattern of the infectious disease among the at least one animal object;

an animal suspected of having the infectious disease extracting unit determining whether the image data of an outward appearance of the at least one candidate object is matched with an external lesion of the infectious disease and extracting the animal suspected of having the infectious disease from the at least one candidate animal object; and a suspected symptom occurrence signal generating unit generating the suspected symptom occurrence signal including the image data on the animal suspected of having the infectious disease when the animal suspected of having the infectious disease is extracted;

confirming, at a second server, an occurrence of the infectious disease by analyzing the image data of the animal suspected of having the infectious disease upon receipt of the suspected symptom occurrence signal from the first server, and transmitting a warning signal when confirmed the occurrence of the infectious disease; and requesting, at a manager terminal, the image data of the animals from the first server upon receipt of the warning signal from the second server and displaying the image data of the animals, wherein the animal image detecting unit generates an edge image using contours of objects in the image data, generates a background edge image using a pre-stored background image of the barn, subtracts the background edge image from the edge image to make a difference image, identifies the at least one animal object by using a scale invariant feature transform (SIFT) or speeded up robust features (SURF) algorithm that extracts feature points from the image data, and detects the at least one animal object using an object detection classifier, wherein the object detection classifier generates a database (DB) for the at least one animal object using at least one of a support vector machine (SVM), neural networks, and an AdaBoost algorithm.

12. The method of claim 11, wherein the candidate object extracting unit calculates an amount of activity of the at least one animal object during a specific time period, and extracts the at least one candidate object having the amount of activity equal to or less than a reference value.

\* \* \* \* \*